United States Patent
Iwabuchi et al.

(10) Patent No.: US 9,522,013 B2
(45) Date of Patent: Dec. 20, 2016

(54) BASKET TYPE GRASPING FORCEPS

(71) Applicant: OLYMPUS CORPORATION, Hachioji-shi, Tokyo (JP)

(72) Inventors: Akihisa Iwabuchi, Higashimatsuyama (JP); Tomotaka Hayakawa, Kawaguchi (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/145,011

(22) Filed: May 3, 2016

(65) Prior Publication Data

US 2016/0242795 A1 Aug. 25, 2016

Related U.S. Application Data

(63) Continuation of application No. PCT/JP2014/079501, filed on Nov. 6, 2014.

(30) Foreign Application Priority Data

Nov. 12, 2013 (JP) .................................. 2013-233973

(51) Int. Cl.
*A61B 17/22* (2006.01)
*A61B 17/221* (2006.01)

(52) U.S. Cl.
CPC ...... *A61B 17/221* (2013.01); *A61B 2017/2212* (2013.01)

(58) Field of Classification Search
CPC ............ A61B 17/32056; A61B 17/221; A61B 2017/2212; A61B 17/22
See application file for complete search history.

(56) References Cited

FOREIGN PATENT DOCUMENTS

| EP | 2 638 870 A1 | 9/2013 |
|---|---|---|
| JP | H11-47141 A | 2/1999 |
| JP | H11-114070 A | 4/1999 |
| JP | 2000-507856 A | 6/2000 |
| JP | 2006-094876 A | 4/2006 |
| JP | 2006-314811 A | 11/2006 |
| WO | 97/35522 A1 | 10/1997 |
| WO | 99/60933 A1 | 12/1999 |
| WO | 2012/141213 A1 | 10/2012 |

OTHER PUBLICATIONS

Feb. 10, 2015 International Search Report issued in International Patent Application No. PCT/JP2014/079501.

*Primary Examiner* — Gregory Anderson
(74) *Attorney, Agent, or Firm* — Oliff PLC

(57) ABSTRACT

Basket type grasping forceps includes sheath, main body section which has distal and proximal end inserted through sheath, and manipulation sections fixed to sheath which proximal end of main body section is attached. Main body section includes basket section provided at distal side of main body section, and is configured to hold foreign substance, first wire provided at proximal side of basket section and is fixed to basket section, and removal mechanism attached to basket section and moves foreign substance in basket section. Basket section includes plurality of basket wires and fixing member. Removal mechanism includes slide sleeve and second wire. Slide sleeve is disposed at distal end of basket section in state which plurality of basket wires are spread, and foreign substance captured by basket section is discharged from opening formed at proximal side, by moving slide sleeve to proximal side and reducing a diameter of basket section.

4 Claims, 10 Drawing Sheets

BASKET TYPE GRASPING FORCEPS

This application is a continuation application, based on PCT/JP2014/079501, filed on Nov. 6, 2014, claiming priority based on Japanese Patent Application No. 2013-233973, filed in Japan on Nov. 12, 2013, the content of which is incorporated herein by reference.

FIELD OF THE INVENTION

The present invention relates to a basket type grasping forceps.

DESCRIPTION OF THE RELATED ART

In the related art, a basket type grasping forceps inserted into a conduit line in a body such as a bile duct or the like and configured to collect a foreign substance such as a calculus or the like is known (for example, see Japanese Unexamined Patent Application, First Publication No. H11-114070, Japanese Unexamined Patent Application, First Publication No. 2006-94876, and International Publication No. PCT/2012/141213).

Since the basket type grasping, forceps has a structure for holding a foreign substance using a plurality of wires, when a large amount of a foreign substance should be collected, a basket may not be removed from the conduit line while holding the foreign substance. For example, when the foreign substance is not removed from between the plurality of wires disclosed in Japanese Unexamined Patent Application, First Publication No. H11-114070, Japanese Unexamined Patent Application, First Publication No, 2006-94876, and International Publication No. PCT/2012/141213, the basket may not be removed from the conduit line.

SUMMARY OF THE INVENTION

Means for Solving the Problem

A basket type grasping forceps of a first aspect of the present invention a sheath, a main body section which has a distal end and a proximal end and inserted through the sheath; and a manipulation section which is fixed to the sheath and to which the proximal end of the main body section is attached. The main body section includes a basket section which is provided at a distal side of the main body section, which has a substantially fusiform shape, and which is configured to hold a foreign substance, a first wire which is provided at a proximal side of the basket section and which is fixed to the basket section, and a removal mechanism which is attached to the basket section and which moves the foreign substance in the basket section. The basket section includes a plurality of basket wires which extend in a helical shape about a central axis of the basket section such that a size of an opening at the proximal side of the basket section is larger than a size of an opening at a distal side of the basket section, and a fixing member which binds and fixes the plurality of basket wires. The removal mechanism includes a slide sleeve through which the plurality of basket wires are inserted and which is configured to advance and retract with respect to the plurality of basket wires, and a second wire which has a distal end fixed to the slide sleeve and which is configured to advance and retract the slide sleeve with respect to the basket wires. The slide sleeve is disposed at a distal end of the basket section in a state in which the plurality of basket wires are spread, and the foreign substance which is captured by the basket section is discharged from the opening formed at the proximal side of the plurality of basket wires, by moving the slide sleeve which is disposed at the distal end of the basket section to the proximal side and reducing a diameter of the basket section from the distal side to the proximal side.

According to a second aspect of the present invention, in the basket type grasping forceps of the first aspect, the main body section may further have a center wire, and the center wire may be fixed to the distal end of the basket section, pass substantially a center of the basket section, and extend to at least the proximal end of the basket section.

According to a third aspect of the present invention, in the basket type grasping forceps of the second aspect, the second wire may extend from the slide sleeve to the proximal side through the basket section.

According to a fourth aspect of the present invention, in the basket type grasping forceps of the third aspect, a lumen may be formed at the slide sleeve and the plurality of basket wires and the center wire may be inserted into the lumen.

DETAILED DESCRIPTION OF THE INVENTION

First Embodiment

Figure 1:
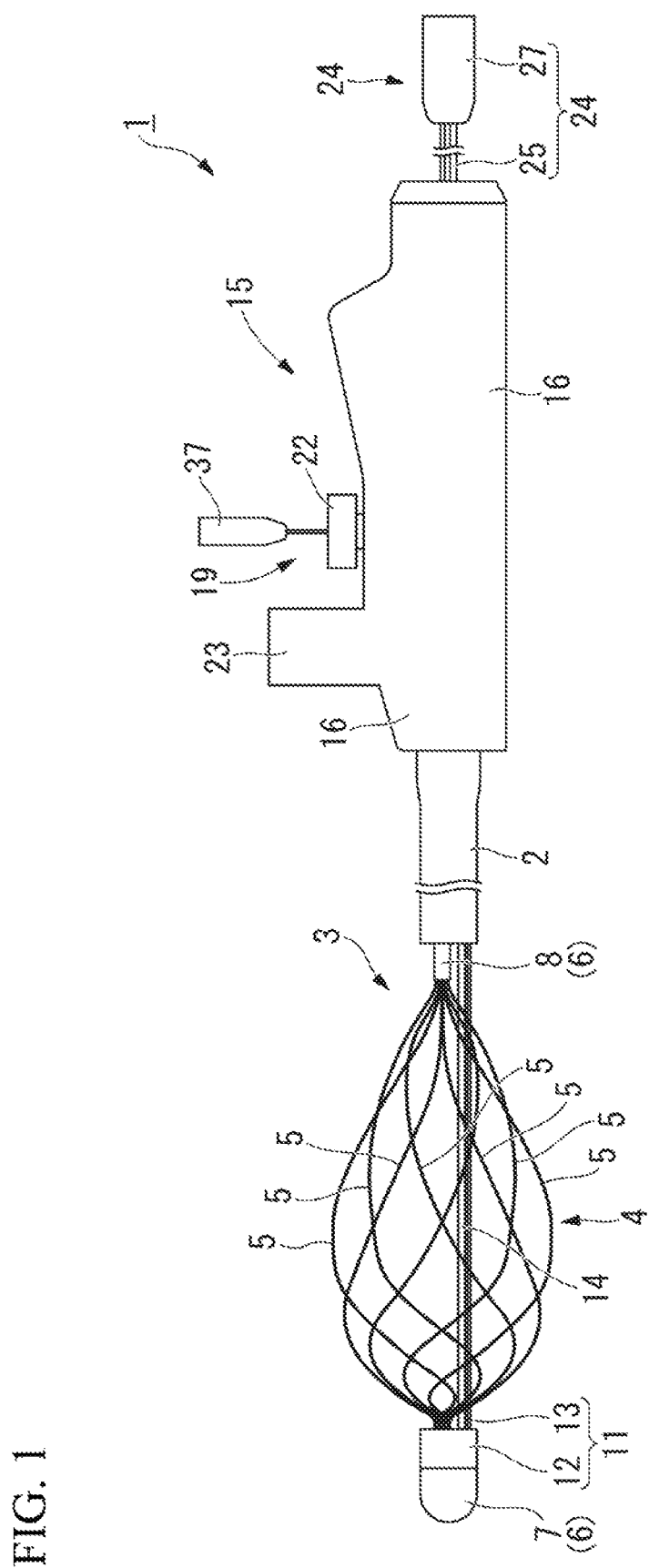
FIG. 1 is a general view of basket type grasping biceps of a first embodiment of the present invention.
Figure 2:
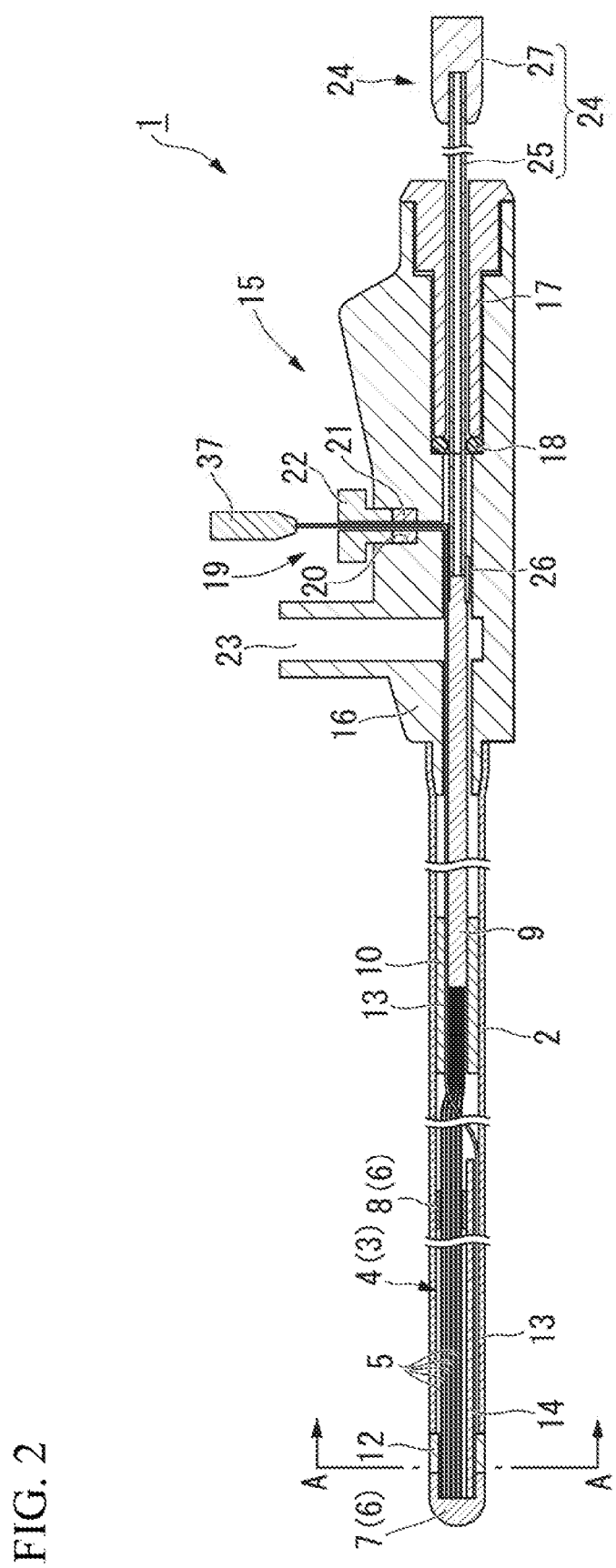
FIG. 2 is a cross-sectional view of the basket type grasping forceps of the embodiment.
Figure 3:
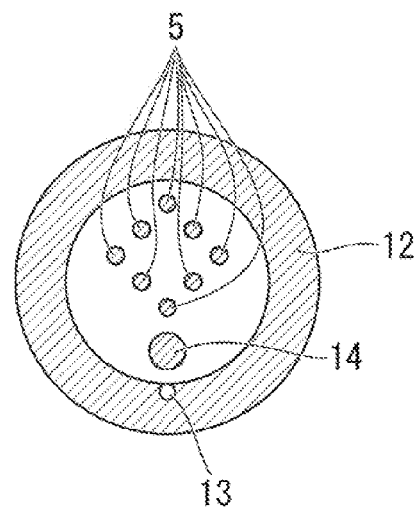
FIG. 3 is a cross-sectional view taken along line A-A of FIG. 2.

A basket type grasping forceps of a first embodiment of the present invention will be described. FIG. 1 is a general view of the basket type grasping forceps of the embodiment. FIG. 2 is a cross-sectional view of the basket type grasping forceps of the embodiment. FIG. 3 is a cross-sectional view taken along line A-A of FIG. 2.

The basket type grasping forceps 1 shown in FIGS. 1 and 2 is a medical instrument inserted into a conduit line in a body such as a bile duct or the like and configured to remove a foreign substance.

As shown in FIG. 1, the basket type grasping forceps 1 includes a sheath 2, a main body section 3 inserted into the sheath 2, and a manipulation section 15 fixed to the sheath 2.

The sheath 2 is a cylindrical member having flexibility. The sheath 2 has an exterior dimension at Which it can be inserted to advance or retreat with respect to a treatment tool channel of the endoscope. A distal end of the sheath 2 has a hardness such that a basket section 4 (to be described below) can be folded upon use of the basket type grasping forceps 1.

As shown in FIG. 2, the main body section 3 is an elongated member inserted into the sheath 2 having a distal end and a proximal end. The main body section 3 includes the basket section 4, a first wire 9 connected to the basket section 4, a connecting member 10 configured to connect the basket section 4 and the first wire 9, a removal mechanism 11 configured to remove a foreign substance in the basket section 4, and a center wire 14 fixed to the basket section 4.

As shown in FIGS. 1 and 2, the basket section 4, which is expandable and contractible, is disposed at a distal end side of the main body section 3 and spread in a substantially fusiform shape to hold a foreign substance. The basket section 4 in a contracted state has a substantially linear shape that can be accommodated in the sheath 2.

The basket section 4 includes a plurality of basket wires 5, and a fixing member 6 configured to fix the plurality of basket wires 5 and form a basket section in a substantially fusiform shape.

Figure 4:
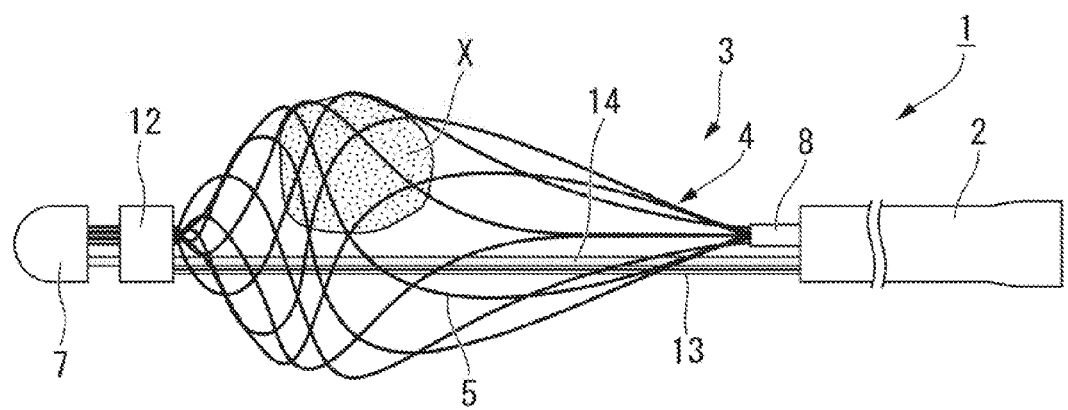
FIG. 4 is a view for describing an action of the basket type grasping forceps of the embodiment.

The basket section 4 has a substantially fusiform shape and holds a foreign substance in the body therein (see FIG. 4). The plurality of basket wires 5 are provided such that the basket section 4 is formed in a substantially fusiform shape.

In the embodiment, the basket wires 5 form a helical shape about a centerline of the basket section 4. The basket wires 5 have a denser helical pitch closer to the distal side. That is, sizes of openings formed by the plurality of basket wires 5 are smallest at the distal end of the basket section 4 and gradually increase toward the proximal side of the basket section 4.

As shown in FIG. 1, the fixing member 6 has a distal fixing member 7 configured to bind the basket wires 5 and fix them to the distal side of the basket section 4, and a proximal fixing member 8 configured to bind the basket wires 5 and fix them to the proximal side of the basket section 4. Both of the distal fixing member 7 and the proximal fixing member 8 form a cylindrical shape.

All of the basket wires 5 are inserted into the distal fixing member 7 and the proximal fixing member 8. The distal fixing member 7 and the basket wires 5 are fixed by a known fixing method such as adhesion, brazing, soldering, welding, or the like. Similarly, the proximal fixing member 8 and the basket wires 5 are fixed by a known fixing method such as adhesion, brazing, soldering, welding, or the like.

As shown in FIG. 2, the first wire 9 is disposed at the proximal side of the basket section 4 and fixed to the basket section 4 by the connecting member 10.

As shown in FIG. 2, a distal end of the first wire 9 is inserted into the connecting member 10, and simultaneously, proximal ends of the basket wires 5 of the basket section 4 are inserted into the connecting member 10. The distal end of the first wire 9 and the connecting member 10 are fixed by a known fixing method such as adhesion, brazing, soldering, welding, or the like. Similarly, the proximal end of the basket wires 5 and the connecting member 10 are fixed by a known fixing method such as adhesion, brazing, soldering, welding, or the like.

The removal mechanism 11 shown in FIG. 1 is installed to move the foreign substance in the basket section 4 from the distal side toward the proximal side of the basket section 4.

As shown in FIGS. 1 and 2, the removal mechanism 11 includes a slide sleeve 12 attached to the basket section 4, and a second wire 13 fixed to the slide sleeve 12.

The slide sleeve 12 is a cylindrical member into which the plurality of basket wires 5 are inserted, and is able to advance or retreat with respect to the plurality of basket wires 5. All of the basket wires 5 are inserted into the slide sleeve 12. The slide sleeve 12 is disposed at the distal end of the basket section 4 in a state in which the plurality of basket wires 5 are spread to form a substantially fusiform shape.

The second wire 13 is a wire-shaped member configured to advance or retract the slide sleeve 12 with respect to the basket wires 5. The distal end of the second wire 13 is fixed to the slide sleeve 12.

In a state in which the basket section 4 forms a substantially fusiform shape, the second wire 13 extends to the proximal side through the basket section 4 to be directed from the slide sleeve 12 to the sheath 2. Further, in the embodiment, the second wire 13 extends to the manipulation section 15 through the sheath 2. A second wire manipulation mechanism 37 is attached to the proximal end of the second wire 13.

The center wire 14 is fixed to the distal end of the basket section 4 and extends to at least the proximal end of the basket section 4 through substantially a center of the basket section 4. In the embodiment, the center wire 14 is fixed to the inside of the distal fixing member 7 of the basket section 4 together with the basket wires 5.

In the embodiment, the proximal end of the center wire 14 extends closer to the proximal side than the opening of the distal end side of the sheath 2, and even in a state in which the basket section 4 is completely exposed from the opening of the distal end of the sheath 2 in a conventional use state of the basket type grasping forceps 1, the proximal end of the center wire 14 is formed not to exit the opening of the distal end side of the sheath 2.

As shown in FIGS. 1 and 2, the manipulation section 15 is fixed to the proximal end of the sheath 2 to advance or retract the first wire 9 and the second wire 13 with respect to the sheath 2.

The manipulation section 15 includes a manipulation main body 16, a slider 24 and the second wire manipulation mechanism 37.

The manipulation main body 16 is fixed to the proximal end of the sheath 2. The manipulation main body 16 has a first port 17 through which a portion of the slider 24 configured to advance and retract the first wire 9 is inserted, and a second port 19 through which the second wire 13 is inserted.

The first port 17 has an O-ring 18 that can be adhered to an niter surface of a shah 25 (to be described below). Accordingly, the first port 17 and the shaft 25 are able to advance and retreat in a water-tight state.

The second port 19 has an opening section 20 in communication with the sheath 2, a stopper 21 having elasticity and disposed in the opening section 20, and a screw body 22 screwed into the opening section 20 of the second port 19 and configured to elastically deform the stopper 21. As the screw body 22 is screwed into the opening section 20, when the stopper 21 is elastically deformed to be adhered to an outer circumferential surface of the second wire 13, the second wire 13 is fixed to the manipulation section 15.

When the stopper 21 is elastically deformed to be adhered to the outer circumferential surface of the second wire 13, the second port 19 is water-tightly closed.

A third port 23 is a port configured to deliver a liquid such as a contrast medium, rinse water, or the like, and can be water-tightly connected to, for example, a syringe.

When the liquid is injected from the third port 23 while the first port 17 and the second port 19 are in the water-tight state, the liquid flows into the sheath 2 to be ejected from an opening, of the distal end side of the sheath 2.

The slider 24 has the shaft 25 fixed to the proximal end of the first wire 9, and a grip 27 disposed at the proximal end of the shaft 25.

The shaft 25 is a hard member, and has a cylindrical shape in the embodiment. The first wire 9 and the shaft 25 are connected via a connecting pipe 26. In the embodiment, the proximal end of the first wire 9 is inserted into the connecting pipe 26 and fixed by a known fixing method such as adhesion, brazing, soldering, welding, or the like. Similarly, the distal end of the shaft 25 is inserted into the connecting pipe 26 and fixed by a known fixing method such as adhesion, brazing, soldering, welding, or the like.

The grip 27 is a member having an exterior shape larger than that of the shaft 25 such that an operator of the basket type grasping forceps 1 can easily hold the grip 27. The grip 27 may have a brace according to necessity.

The second wire manipulation mechanism 37 is attached to the proximal end of the second wire 13. As the second wire manipulation mechanism 37 is manipulated, the slide sleeve 12 and the second wire 13 can advance and retreat with respect to the plurality of basket wires 5.

Figure 5:
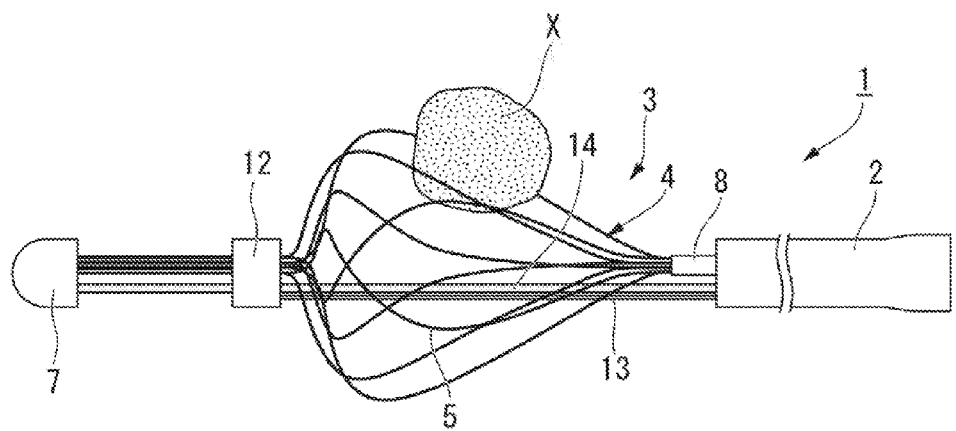
FIG. 5 is a view for describing an action of the basket type grasping forceps of the embodiment.

Next, an action of the basket type grasping forceps 1 of the embodiment will be described. FIGS. 4 and 5 are views for describing, the action of the basket type grasping forceps of the embodiment.

Like the general basket type medical treatment tool, the basket type grasping forceps 1 is inserted into the conduit line such as the bile duct or the like in the body of the patient through the endoscope channel in a state in which the basket section 4 is accommodated in the sheath 2. When the basket section 4 protrudes from the sheath 2 in the conduit line due to the advance manipulation of the slider 24, the basket section 4 is widened and opened by an elastic force of the basket wires 5.

After a foreign substance X such as renal calculi or the like is taken into the widened and opened basket section 4, the slider 24 can be pulled to reduce a diameter of the basket section 4 and the foreign substance X can be tightly held in the basket section 4. After that, the basket type grasping forceps 1 is removed from the body of the patient together with the endoscope, and the foreign substance X is collected.

When the foreign substance X held in the basket section 4 is large, the basket section 4 may not be removed from the conduit line such as the bile duct or the like. In order to avoid this, in a state in which the basket section 4 is disposed in the conduit line, the held foreign substance X should be discharged to the outside of the basket.

As a method of discharging the foreign substance X in the related art, there is a method of introducing an emergency lithotripter a laser, or the like, into the body and breaking the foreign substance X, or the like. However, these methods in the related art are complicated and increase the entire treatment time.

In the basket type grasping forceps 1, when the proximal end of the second wire 13 in the second wire manipulation mechanism 37 shown in FIG. 1 is pulled to the proximal side, the slide sleeve 12 disposed at the distal end of the basket section 4 is pulled to the proximal side. Accordingly, as shown in FIG. 5, the slide sleeve 12 is moved to the proximal side with respect to the basket section 4.

The slide sleeve 12 moved from the distal end of the basket section 4 to the proximal side moves the basket wires 5 such that each of the basket wires 5 approaches with each other. That is, as the slide sleeve 12 is moved to the proximal side, a diameter of the basket section 4 is gradually reduced from the distal side to the proximal side.

When the diameter of the basket section 4 is gradually reduced from the distal side to the proximal side, in the case in which the foreign substance X in the body is captured by the distal side portion of the basket section 4, the foreign substance X is moved to the proximal side in the basket section 4.

When a size of the opening of the distal side of the basket section 4 of the embodiment is compared with that of the opening of the proximal side, the opening of the proximal side is larger. For this reason, according to a decrease in diameter of the basket section 4, the foreign substance X moved to the proximal side in the basket section 4 is discharged to the outside of the basket section 4 from the gap between the basket wires 5.

In these points, the basket type grasping forceps 1 of the embodiment can remove the therein substance X in the body to the outside of the basket section 4 by moving the slide sleeve 12 from the distal end of the basket section 4 to the proximal side. As a result, the basket type grasping forceps 1 of the embodiment can easily remove the foreign substance X held in the basket wires 5, and efficiency of treatment can be increased.

(Variant 1-1)

Figure 6:
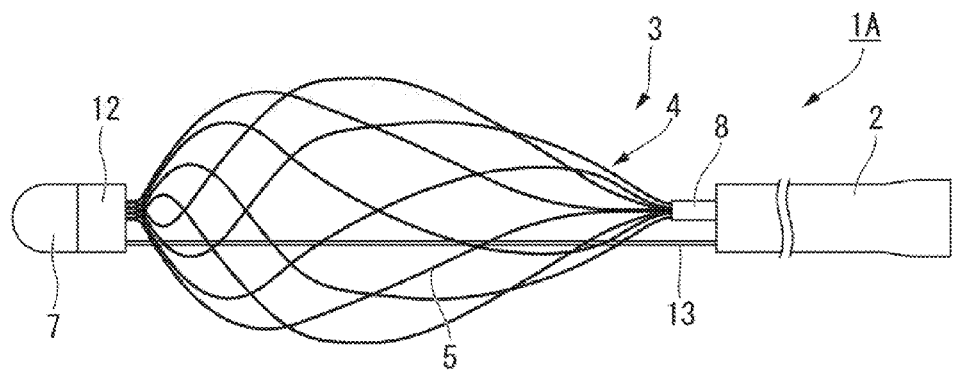
FIG. 6 is a side view showing a configuration of a variant of the embodiment.

Next, a variant of the basket type grasping forceps of the embodiment will be described. FIG. 6 is a side view showing a configuration of the variant.

As shown in FIG. 6, the basket type grasping forceps 1A of the variant does not include the center wire 14.

Like the basket type grasping forceps 1 of the above-mentioned first embodiment, even in the basket type grasping forceps 1A of the variant, as the slide sleeve 12 is moved from the distal end of the basket section 4 to the proximal side, a diameter of the basket section 4 is gradually reduced from the distal side to the proximal side.

For this reason, the basket type grasping forceps 1A of the variant also exhibits the same effect as the first embodiment.

(Variant 1-2)

Figure 7:
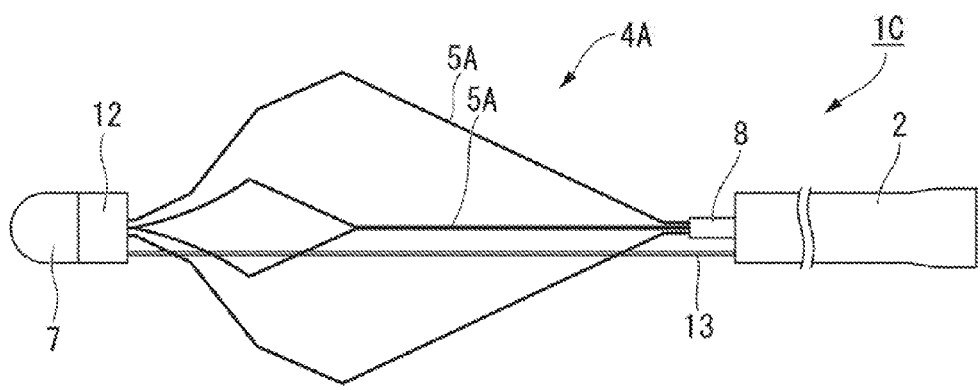
FIG. 7 is a side view showing a configuration of another variant of the embodiment.

Next, another variant of the basket type grasping forceps 1 of the first embodiment will be described. FIG. 7 is a side view showing a configuration of the variant.

As shown in FIG. 7, a basket type grasping forceps 1C of the variant has a basket section 4A having a different shape from the first embodiment.

The basket section 4A has a plurality of basket wires 5A in which two element wires are bound at the proximal side and branched off from the intermediate portion toward the distal side one by one. In the basket section 4A of the variant, as the basket wires 5A have branches, the opening is reduced at the distal side and the opening is increased at the proximal side.

Even in the basket type grasping forceps 1C of the variant, similar to the basket type grasping forceps 1 of the first embodiment, as the slide sleeve 12 is moved from the distal end of the basket section 4A to the proximal side, a diameter of the basket section 4A is gradually reduced from the distal side to the proximal side.

For this reason, the basket type grasping forceps 1A of the variant also exhibits the same effect as the first embodiment.

Second Embodiment

Figure 8:
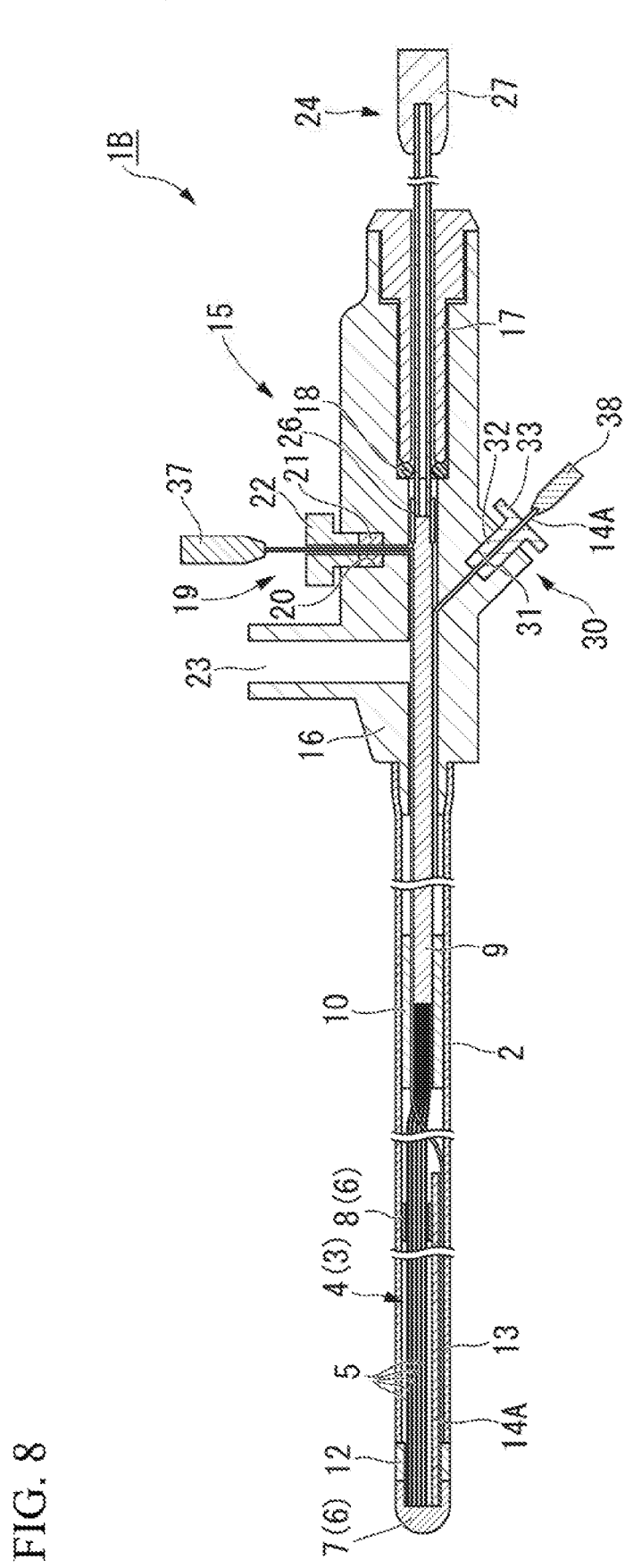
FIG. 8 is a cross-sectional view show a basket type grasping forceps of a second embodiment of the present invention.

Next, the basket type grasping forceps of the second embodiment of the present invention will be described. FIG. 8 is a cross-sectional view showing a configuration of the basket type grasping forceps of the embodiment.

As shown in FIG. 8, the basket type grasping forceps 18 of the embodiment has a center wire 14A extending to the manipulation section 15, instead of the center wire 14 described in the first embodiment.

A fourth port 30 is installed, at the manipulation section 15. The center wire 14A is inserted through the fourth port 30, the proximal end of the center wire 14A is pulled out to the outside of the manipulation section 15, and the center wire manipulation mechanism 38 is attached to the fourth port 30.

The fourth port 30 installed at the manipulation section 15 of the embodiment includes an opening section 31 through which the center wire 14 is inserted, a stopper 32 constituted by an elastic member formed in the opening section, and a screw body 33 screwed into the opening section 31 to deform the stopper 32.

When the screw body 33 in the fourth port 30 is screwed into the opening section 31, the stopper 32 is elastically deformed to come in contact with the outer surface of the center wire 14A, and the opening section 31 is water-tightly closed while the center wire 14A is fixed to the manipulation section 15. Accordingly, the liquid can be delivered from the third port 23 to the distal end of the sheath 2.

In the embodiment, it is possible to manipulate the center wire 14A by a center wire manipulation mechanism 38. For this reason, a shape of the basket section 4 can be varied by advancing and retracting the center wire 14A in a longitudinal direction of the sheath 2 in the center wire manipulation mechanism 38.

Third Embodiment

Figure 9:
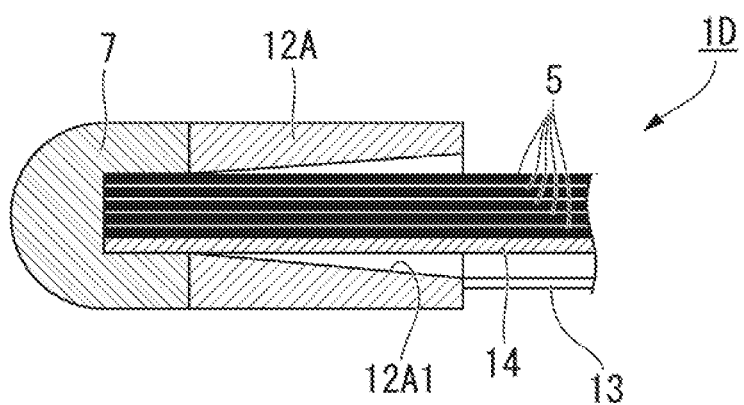
FIG. 9 is a cross-sectional view showing a basket type grasping forceps of a third embodiment of the present invention.

Next, a basket type grasping forceps of a third embodiment of the present invention will be described. FIG. 9 is a cross-sectional view showing a configuration of the embodiment.

As shown in FIG. 9, the embodiment is distinguished from the first embodiment in that a slide sleeve 12A having a different shape from that of the slide sleeve 12 described in the first embodiment is provided.

The slide sleeve 12A installed at the basket type grasping forceps 110 of the embodiment has an inner diameter having, a slight clearance with respect to a diameter of a bundle when the basket wires 5 are bound to be closely adhered to each other at the distal side. The slide sleeve 12A has an inner diameter at the proximal side larger than an inner diameter of the distal side.

That is, the slide sleeve 12A of the embodiment has a tapered inner surface 12A1 having an inner diameter that is gradually increased from the distal side to the proximal side.

In the embodiment, when the slide sleeve 12A is moved from the distal side to the proximal side of the basket section 4, a contact angle of the inner surface of the slide sleeve 12A with respect to the basket wires 5 radially extending from a centerline of the slide sleeve 12A can be reduced. For this reason, the slide sleeve 12A can be smoothly moved to the proximal side with respect to the basket wires 5.

A shape of the inner surface of the slide sleeve 12A is not limited to the tapered shape. For example, grooves configured to individually guide the basket wires 5 may be formed in the inner surface of the slide sleeve 12A. In this case, the basket wires 5 cannot be easily entangled in the slide sleeve 12A and can smoothly move the slide sleeve 12A with respect to the basket wires 5.

Fourth Embodiment

Figure 10:
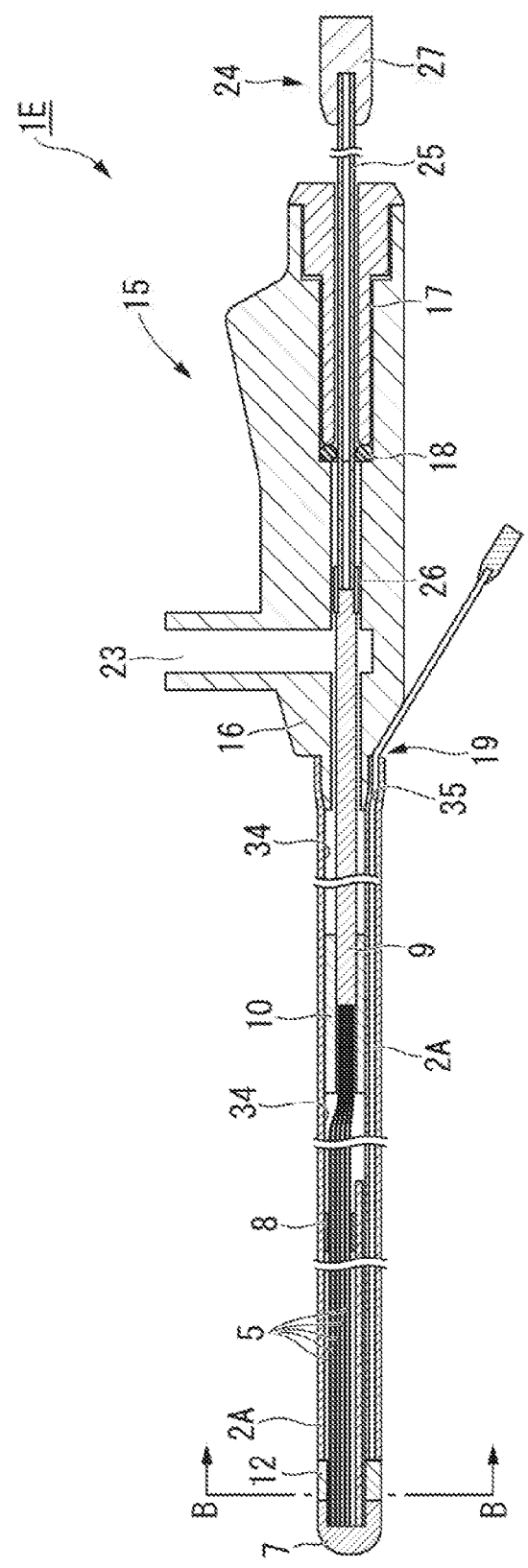
FIG. 10 is a cross-sectional view showing a basket type grasping forceps of fourth embodiment of the present invention.
Figure 11:
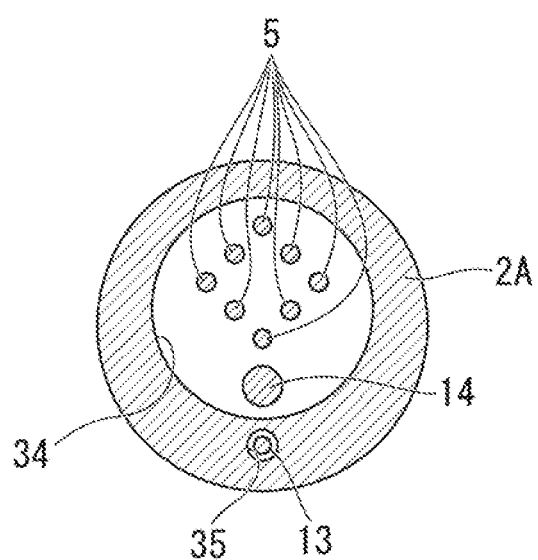
FIG. 11 is a cross-sectional view taken along line B-B of FIG. 10.

Next, a basket type grasping forceps of a fourth embodiment of the present invention will be described. FIG. 10 is a cross-sectional view showing a configuration of the embodiment. FIG. 11 is a cross-sectional view taken along line B-B of FIG. 10.

As shown in FIGS. 10 and 11, the basket type grasping forceps 1E of the embodiment includes a sheath 2A in which a first lumen 34 through which the first wire 9 and the basket section 4 pass, and a second lumen 35 through which the second wire 13 passes are formed, instead of the sheath 2 described in the first embodiment, in the embodiment, the center wire 14 is inserted through the first lumen 34 of the sheath 2A together with the first wire 9 and the basket section 4.

In the embodiment, in the manipulation section 15, the first port 17 comes in communication with the first lumen 34 and the second port 19 comes in communication with the second lumen 35. In the embodiment the second port 19 may not be water-tight since the liquid from the third port 23 does not enter the second port 19.

In the embodiment, while an example in which the third port 23 comes in communication with the first lumen 34 is provided, the third port 23 may come in contact with the second lumen 35.

Even in the above-mentioned configuration, the same effect as the first embodiment is exhibited.

In the embodiment, since the sheath 2A has a plurality of lumens and the first wire 9 and the second wire 13 are inserted into different lumens, the first wire 9 and the second wire 13 are not entangled.

(Variant 4-1)

Figure 12:
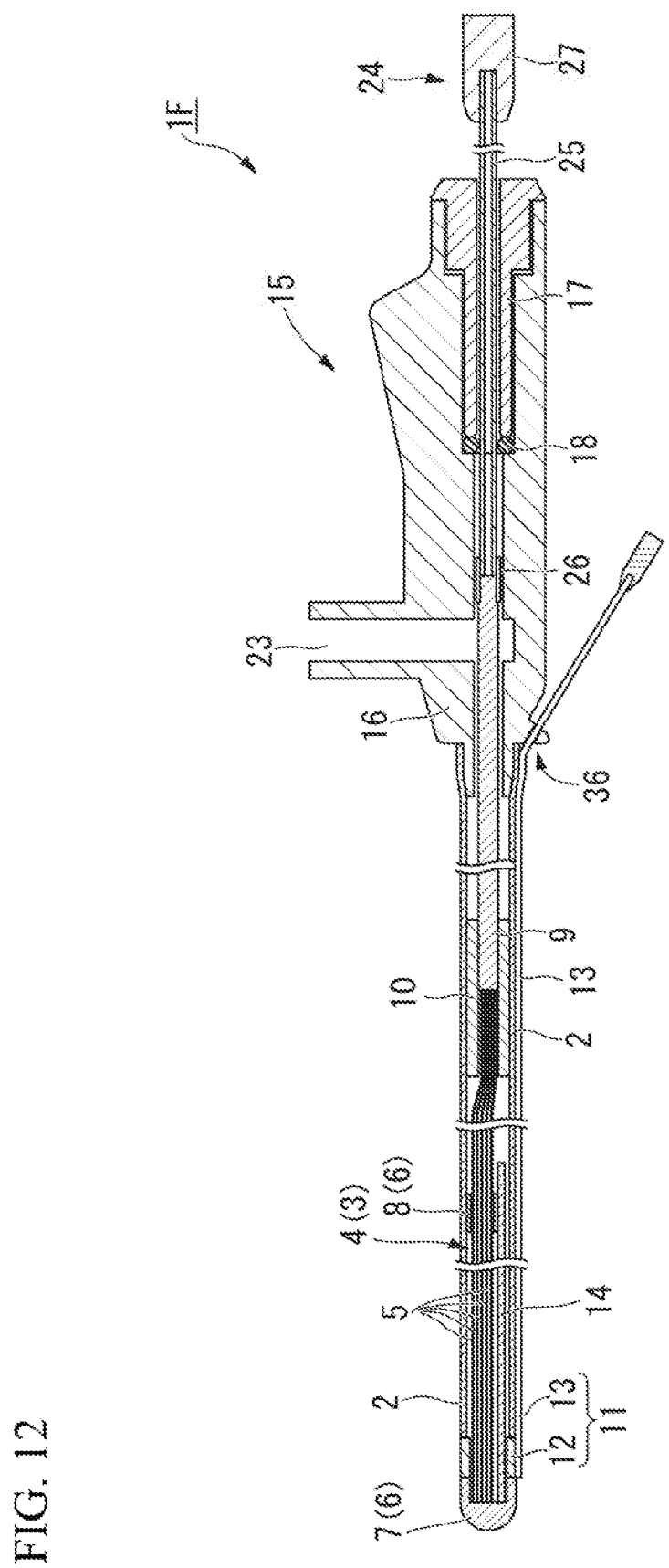
FIG. 12 is a cross-sectional view showing a configuration of the variant of the embodiment.

Next, another variant of the basket type grasping forceps of the fourth embodiment will be described. FIG. 12 is a cross-sectional view showing a configuration of the variant.

As shown in FIG. 12, in the basket type grasping forceps 1F of the variant, the second wire 13 extends toward the manipulation section 15 outside the sheath 2. The manipulation section 15 has a hook 36 configured to hook the second wire 13, instead of the second port 19.

Even in the above-mentioned configuration, the same effect as the fourth embodiment is exhibited.

In the variant, a means configured to cause the second wire 13 to approach the outer surface of the sheath 2 and hold the second wire 13 may be provided.

While the embodiments and the variants thereof of the present invention have been described above in detail with reference to the accompanying drawings, the specific configuration is not limited to the embodiment but may include design changes without departing from the spirit of the present invention.

Components shown in the above-mentioned embodiments and variants thereof may be appropriately combined and configured.

According to the embodiments, it is possible to provide the basket type grasping forceps capable of easily discharging a foreign substance held in the basket to the outside of the basket.

What is claimed is:
1. A basket type grasping forceps comprising:
a sheath;

a main body section which has a distal end and a proximal end and inserted through the sheath; and a manipulation section which is fixed to the sheath and to which the proximal end of the main body section is attached, wherein the main body section includes:

a basket section which is provided at a distal side of the main body section, which has a substantially fusiform shape, and which is configured to hold a foreign substance;

a first wire which is provided at a proximal side of the basket section and which is fixed to the basket section; and a removal mechanism which is attached to the basket section and which moves the foreign substance in the basket section, the basket section includes:

a plurality of basket wires which extend in a helical shape about a central axis of the basket section such that a size of an opening at the proximal side of the basket section is larger than a size of an opening at a distal side of the basket section; and a fixing member which binds and fixes the plurality of basket wires, and the removal mechanism includes:

a slide sleeve through which the plurality of basket wires are inserted and which is configured to advance and retract with respect to the plurality of basket wires; and a second wire which has a distal end fixed to the slide sleeve and which is configured to advance and retract the slide sleeve with respect to the basket wires, wherein the slide sleeve is disposed at a distal end of the basket section, proximal to the fixing member, in a state in which the plurality of basket wires are spread, and wherein the slide sleeve is configured to discharge the foreign substance held in the basket from the opening formed at the proximal side of the plurality of basket wires by moving the slide sleeve from the distal end of the basket section to the proximal side, thereby reducing a diameter of the basket section from the distal end to the proximal side.

2. The basket type grasping forceps according to claim 1, the main body section further comprising: a center wire, wherein the center wire is fixed to the distal end of the basket section, passes substantially a center of the basket section, and extends to at least the proximal end of the basket section.

3. The basket type grasping forceps according to claim 2, wherein the second wire extends from the slide sleeve to the proximal side through the basket section.

4. The basket type grasping forceps according, to claim 3, wherein a lumen is formed at the slide sleeve and the plurality of basket wires and the center wire are inserted into the lumen.

* * * * *